(12) United States Patent
Abe et al.

(10) Patent No.: US 7,660,618 B2
(45) Date of Patent: Feb. 9, 2010

(54) MAGNETIC RESONANCE IMAGING DEVICE

(75) Inventors: Takayuki Abe, Matsudo (JP); Shigeru Watanabe, Moriya (JP)

(73) Assignee: Hitachi Medical Corporation, Tokyo (JP)

( * ) Notice: Subject to any disclaimer, the term of this patent is extended or adjusted under 35 U.S.C. 154(b) by 770 days.

(21) Appl. No.: 10/517,102

(22) PCT Filed: Jun. 5, 2003

(86) PCT No.: PCT/JP03/07126

§ 371 (c)(1),
(2), (4) Date: Dec. 7, 2004

(87) PCT Pub. No.: WO03/103491

PCT Pub. Date: Dec. 18, 2003

(65) Prior Publication Data
US 2005/0177042 A1 Aug. 11, 2005

(30) Foreign Application Priority Data

Jun. 7, 2002 (JP) ............................. 2002-166823
Jul. 12, 2002 (JP) ............................. 2002-203894

(51) Int. Cl.
*A61B 5/055* (2006.01)
(52) U.S. Cl. ...................................... 600/410; 600/420
(58) Field of Classification Search .......... 600/410–423
See application file for complete search history.

(56) References Cited

U.S. PATENT DOCUMENTS 4,830,012 A * 5/1989 Riederer ..................... 600/410
5,045,791 A * 9/1991 Yamamoto et al. .......... 324/309
5,474,067 A * 12/1995 Laub .......................... 600/413

(Continued)

FOREIGN PATENT DOCUMENTS

JP  5-137709  6/1993

(Continued)

OTHER PUBLICATIONS

Mar. 18, 2008 Japanese official action in connection with corresponding Japanese application No. 2002-203894.

*Primary Examiner*—Brian Casler
*Assistant Examiner*—Peter Luong
(74) *Attorney, Agent, or Firm*—Cooper & Dunham LLP

(57) ABSTRACT

An MRI apparatus having a pulse sequence of dynamic MRA performs a pulse sequence for monitoring arrival of a contrast agent at a blood vessel of interest. The pulse sequence is substantially the same as the imaging sequence except that the phase-encode number and/or the slice-encode number is small. A time-series image reconstructed by using data measured under the condition of applying gradient magnetic fields with a low spatial resolution is displayed to ascertain that the contrast agent has arrived at the blood vessel of interest. When the contrast agent arrives at the blood vessel of interest, the phase-encode and slice-encode are added to continue the substantial measurement pulse sequence without changing the pulse sequence itself. The first image of the substantial measurement is produced by using the data acquired at the time of arrival of the contrast agent in monitoring. Thus, the arrival time of the contrast agent can be reliably monitored with high time-resolution and the substantial measurement can be performed with most suitable timing to obtain an excellent blood vessel image.

12 Claims, 7 Drawing Sheets

U.S. PATENT DOCUMENTS

| | | | |
|---|---|---|---|
| 5,485,086 A * | 1/1996 | Meyer et al. | 324/307 |
| 5,713,358 A * | 2/1998 | Mistretta et al. | 600/420 |
| 5,798,642 A * | 8/1998 | Watanabe | 324/307 |
| 5,827,187 A * | 10/1998 | Wang et al. | 600/419 |
| 5,897,496 A * | 4/1999 | Watanabe | 600/413 |
| 6,044,290 A * | 3/2000 | Vigen et al. | 600/419 |
| 6,097,185 A * | 8/2000 | Watanabe et al. | 324/309 |
| 6,195,579 B1 * | 2/2001 | Carroll et al. | 600/420 |
| 6,222,365 B1 * | 4/2001 | Taniguchi et al. | 324/309 |
| 6,459,264 B1 * | 10/2002 | Fain et al. | 324/307 |
| 6,577,127 B2 * | 6/2003 | Harvey et al. | 324/307 |
| 6,603,992 B1 * | 8/2003 | Debbins et al. | 600/420 |
| 6,639,211 B1 * | 10/2003 | Anand et al. | 250/282 |
| 6,690,961 B1 * | 2/2004 | Kaufman et al. | 600/410 |
| 6,946,836 B2 * | 9/2005 | Kuhara | 324/307 |
| 6,968,225 B2 * | 11/2005 | Vu | 600/410 |

FOREIGN PATENT DOCUMENTS

| | | |
|---|---|---|
| JP | 2000/237163 | 9/2000 |
| JP | 2001-276016 | 10/2001 |
| WO | WO00/40990 A1 | 7/2000 |
| WO | WO02/04970 A1 | 1/2002 |
| WO | WO 0204970 A1 * | 1/2002 |

* cited by examiner

MAGNETIC RESONANCE IMAGING DEVICE

TECHNICAL FIELD

The present invention relates to a magnetic resonance imaging apparatus (MRI apparatus) for obtaining a desired tomogram of an object to be examined by utilizing nuclear magnetic resonance (NMR). In particular, it relates to a technique for determining an accurate time of starting a measurement in contrast enhanced angiography.

PRIOR ART

In imaging blood vessels using an MRI apparatus, a method that uses a contrast agent is called contrast enhanced MR angiography (MRA). In particular, the method of continuously performing contrast enhanced MRA for a plurality of phases is called dynamic MRA. In dynamic MRA, a plurality of phases are measured within a short period after injection of a contrast agent, starting from arrival of blood containing the contrast agent at an artery of interest and ending when the blood returns to a vein. It is very important to ascertain the time point when the measurement should be started, that is, the time point when the blood containing the contrast agent arrives at the artery of interest.

As a method of determining the measurement timing in the contrast enhanced MRA, there are known 1) a test injection method and 2) a fluoroscopic trigger method, as set out in, for example, "3D Contrast MR Angiography $2^{nd}$ edition, Prince M R, Grist T M and Debatin J F, Springer, pp 3-39, 1988".

In the test injection method, a small amount of a contrast agent is injected into a patient prior to the actual measurement and the arrival time of the contrast agent at blood vessel of interest is measured beforehand. In the fluoroscopic trigger method, arrival of the contrast agent at the subject blood vessel is observed under fluoroscopy using two-dimensional imaging having a short measurement time, and three-dimensional actual imaging (substantial imaging) is started simultaneously with the arrival of the contrast agent. In this case, an ROI (Region of Interest) is set in a region including the artery of interest and the measurement timing is automatically determined.

In these conventional methods of determining the measurement timing, the contrast agent arrival time is measured by analyzing the intensity of a signal from the ROI in the region of interest. However, the method utilizing analysis of signal intensity from the ROI involves the following problem. If the ROI is outside the measurement plane owing to body movement of the object to be examined (patient), it becomes difficult to ascertain the density change of the contrast agent accurately. As a result, the start timing of the actual (substantial) measurement cannot be determined accurately.

SUMMARY

This disclosure includes an approach to ascertain the timing for beginning an actual measurement (substantial measurement) after injection of a contrast agent when blood vessel imaging is performed in an MRI apparatus.

In an aspect of this disclosure, there is provided a magnetic resonance imaging apparatus comprising an imaging means for applying high-frequency magnetic fields and gradient magnetic fields to an object to be placed in a static magnetic field in accordance with a pulse sequence of dynamic measurement for continuously obtaining a plurality of time-series images and for measuring NMR signals emitted from the object to be examined, a signal processing means for forming images of a desired tissue of the object to be examined from the NMR signals, a display means for displaying the images and a control means for controlling the imaging means and the signal processing means, wherein the imaging means is provided with a monitoring mode in which a desired slab of the object to be examined is measured using a pulse sequence for the dynamic measurement under a condition of applying gradient magnetic fields with a low spatial resolution and a substantial measurement mode in which the same slab is measured using the same pulse sequence under a condition of applying gradient magnetic fields with a high spatial resolution, the control means has a mode switching means for switching from the monitoring mode to the substantial measurement mode and the switching means switches the monitoring mode to the substantial measurement mode with desired timing during the monitoring mode is performed.

Since the region to be examined stays within the slab (a thick slice) even if the subject moves, the region can be observed in the monitoring mode and switching to the substantial measurement mode can be performed with accurate timing. Since the pulse sequence used in the monitoring mode and that used in the substantial measurement mode are the same, no delay occurs for mode switching. In addition, measurement is carried out under low spatial resolution in the monitoring mode, so that the acquisition time for each image is shortened and the time resolution of the monitoring is improved.

According to a preferred embodiment, there is provided means for extracting reference data from the dynamic measurement data acquired in the monitoring mode and temporal change of the extracted reference data is displayed on the displaying means.

This makes it possible to visually discern temporal change of images in association with the temporal change of the reference data.

According to a preferred embodiment, the mode switching means switches from the monitoring mode to the substantial measurement mode when the extracted reference data or change of the reference data reaches a predetermined threshold value.

This enables the mode to be automatically switched based on actually acquired data. As a result, the time for mode switching can be accurately determined corresponding to change of measurement conditions such as difference between individual objects to be examined and difference between measurements.

According to a preferred embodiment, the reference data is, among the NMR signals acquired in the monitoring mode, a signal value of the origin of the k-space or an integration of data in the frequency encoding direction including the origin of the k-space.

Since the signal value of the origin of the k-space always has the highest intensity and reflects the signal intensity of the image, change of the signal intensity can be detected and the precise timing for mode switching can be found automatically.

According to a preferred embodiment, the reference is, among the NMR signals acquired in the monitoring mode, a difference of a signal value of the origin of the k-space or an integration of data in the frequency encoding direction including the origin of the k-space from the corresponding value acquired at the beginning of the monitoring mode.

Since signals from a portion which did not change from the monitoring mode are eliminated and signals from a changed portion can be solely acquired, the timing for mode switching can be determined automatically with still higher precision.

According to a preferred embodiment, the control means controls the signal processing means, when images are reconstructed immediately after the substantial measurement mode begins, so as to reconstruct images using data including data acquired in the pulse sequence performed previously.

Since the pulse sequence used in the monitoring mode is substantially the same as that in the substantial measurement mode, data measured in the monitoring mode is utilized for data of the substantial measurement mode. This enables display of images immediately after the beginning of the substantial measurement.

According to a preferred embodiment, when data of the time-series images is three-dimensional data, it is transformed to a two-dimensional projected image and displayed on the display means.

This makes it possible to show a three-dimensional change on a two-dimensional projected image and facilitates detection of change of a three-dimensional image integrated into two dimensions.

According to a preferred embodiment, the mode switching means has an input means for mode switching and the monitoring mode is switched to the substantial measurement mode by directly inputting a switching instruction to the mode switching means.

An operator can make an instruction of switching mode at a proper time while monitoring the reference data or time-series images displayed in the monitoring mode.

According to a preferred embodiment, the gradient magnetic fields include a slice encode, a phase encode and a frequency encode for the two-dimensional or three dimensional measurement, and under the condition of applying gradient magnetic fields with low spatial resolution one or both of the slice encode and the phase encode is omitted and under the condition of applying gradient magnetic fields with high spatial resolution one or both of the slice encode and the phase encode is imparted.

The two-dimensional or three-dimensional slab image can be projected to a one-dimensional or two-dimensional image while ensuring a sufficient resolution capable of recognizing a region of interest and thus the time of acquiring an image in the monitoring mode can be shortened. As a result, the timing for mode switching can be more accurately determined.

According to a preferred embodiment, the dynamic measurement performed by the imaging means is blood imaging for observing a change of blood flow using a contrast agent, where the slice encode is omitted in the monitoring mode to obtain two-dimensional images and the slice encode is added in the monitoring mode to obtain three-dimensional images.

According to this embodiment, accurate mode-switching can be carried out in dynamic MRA also.

According to a preferred embodiment, a difference image between the blood images obtained before and after injection of the contrast agent is displayed on the displaying means.

This makes it possible to clearly show the flow of the contrast agent.

PREFERRED EMBODIMENTS OF THE INVENTION

Embodiments of the present invention will be explained hereinafter.

Figure 1:
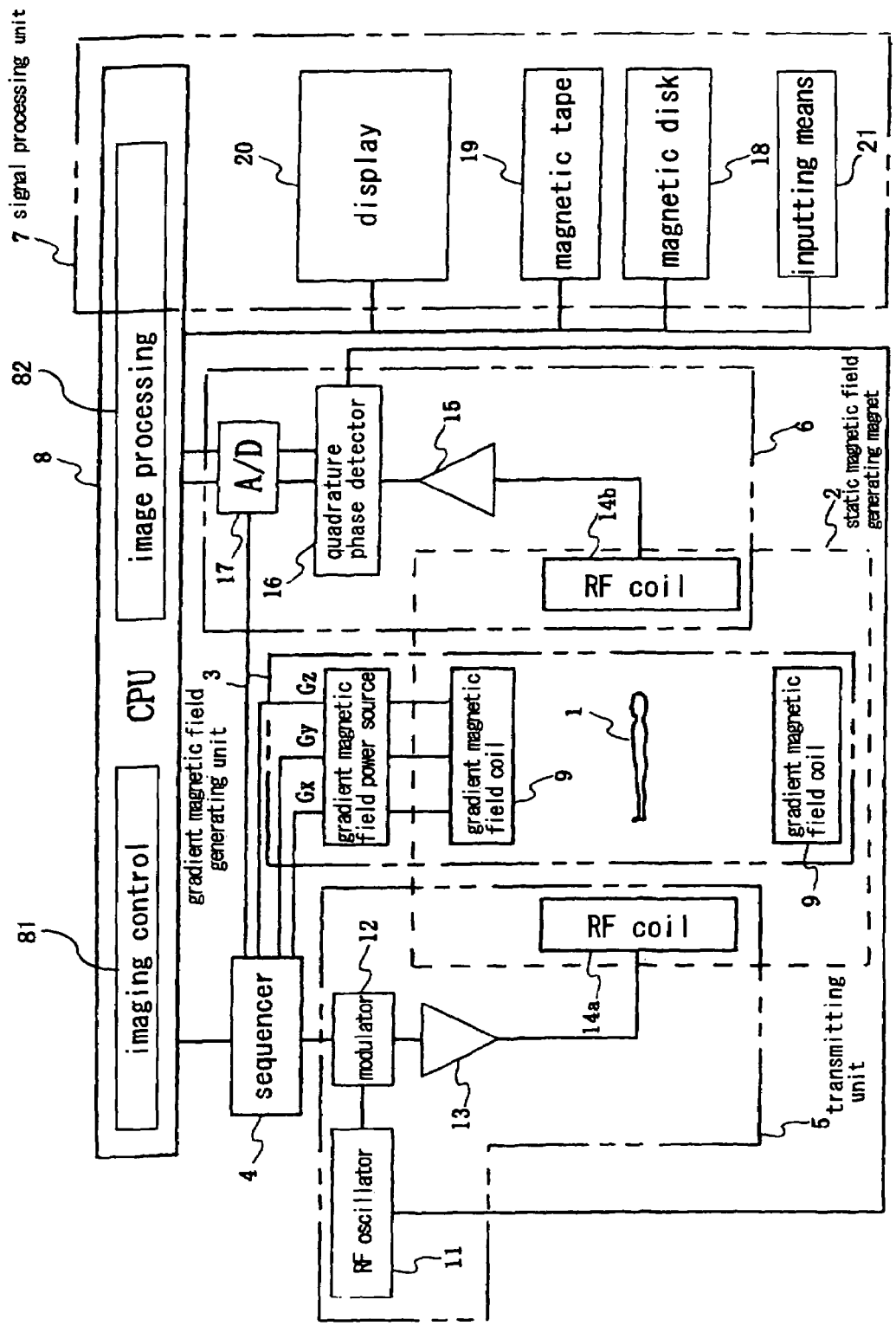
FIG. 1 is an overall block diagram of an MRI apparatus to which the present invention is applied.

FIG. 1 is an overall block diagram showing a configuration of an MRI apparatus to which the present invention is applied. The MRI apparatus comprises mainly a static magnetic field generating magnet 2 that generates a uniform static magnetic field in a space where an object to be examined (patient) 1 is placed, a gradient magnetic field generating unit 3 that imparts gradient magnetic fields to the static magnetic field, a transmitting unit 5 that generates a radio frequency magnetic field to cause nuclear magnetic resonance in atomic nuclei (protons) constituting tissues of the object to be examined 1, a receiving unit 6 that receives echo signals emitted from the object by nuclear magnetic resonance, a signal processing unit 7 that processes echo signals received by the receiving unit 6 and produces images showing a spatial density of the aforementioned atomic nuclei and a spectrum, a central processing unit (CPU) 8 that performs various operations in the signal processing unit 7 and controls the overall operation of the apparatus.

The static magnetic field generating magnet 2 consists of a permanent magnet, a resistive magnet or a super-conductive magnet and produces a uniform static magnetic field around the object in a direction parallel or perpendicular to the body axis of the patient. The gradient magnetic fields generating unit 3 comprises gradient magnetic field generating coils 9 wound in the directions of three axes x, y, z and a gradient magnetic field power source 10 for driving the gradient magnetic field generating coils. Gradient magnetic fields Gx, Gy, and Gz in the three directions x, y, z are applied to the object by driving the gradient magnetic field power source 10 in accordance with instructions from a sequencer 4, which will be explained below. Imaging region (slice, slab) of the object 1 is determined by applying the gradient magnetic fields and position information such as phase-encode and frequency-encode can be imparted to echo signals.

The transmitting unit 5 applies a radio frequency magnetic field to cause nuclear magnetic resonance of nuclei of atoms constituting the living tissues of the object by radio frequency pulses sent from a radio frequency coil 14a, and consists of a radio frequency oscillator 11, a modulator 12, a radio frequency amplifier 13 and the radio frequency coil 14a as a transmitter. In the transmitting unit 5, a radio frequency pulse output from the radio frequency oscillator 11 is amplitude-modulated by the modulator 12, amplified by the radio frequency amplifier 13 and supplied to the radio frequency coil 14a to apply radio frequency magnetic fields (electromagnetic waves) to the object 1.

The receiving unit 6 detects echo signals (NMR signals) emitted from the object 1 by nuclear magnetic resonance, and consists of a radio frequency coil 14b as a receiver, an amplifier 15, a quadrature phase-detector 16 and an A/D converter 17. In the receiving unit 6, echo signals detected by the radio frequency coil 14b are input into the A/D converter 17 via the amplifier 15 and the quadrature phase-detector 16, and converted into digital signals and sent to the signal processing unit 7 as two series of collected data.

The signal processing unit 7 consists of CPU 8 having an image processing section 81 and an imaging control section 82, memory devices such as a magnetic disk 18 and magnetic tape 19, a display such as a CRT 20. Processing including the Fourier transform, correction coefficient calculation and image reconstruction is performed by the image processing section 81 of CPU 8 and the produced image is displayed on the display (monitor) 20. The signal processing unit 7 is also equipped with an input means 21 for inputting conditions of processing, data for processing and the like.

The imaging control section 82 of the CPU 8 sends various instructions necessary for collecting data of tomograms of the object 1 to the gradient magnetic field generating unit 3, the transmitting unit 5 and the receiving unit 6 through the sequencer 4. The sequencer 4 controls the gradient magnetic field generating unit 3, the transmitting unit 5 and the receiving unit 6 to collect necessary data for image reconstruction in accordance with a pulse sequence, which is a timing chart of control predetermined by the imaging method. The imaging control section 82 also controls conditions of applying gradient magnetic fields upon performing a predetermined pulse sequence and switching of imaging modes.

Pulse sequences of the MRI apparatus of the present invention include a pulse sequence of dynamic measurement, where a plurality of time-series images are acquired continuously, for example, a pulse sequence for blood imaging. These pulse sequences are loaded in the CPU 8 as program.

Figure 2:
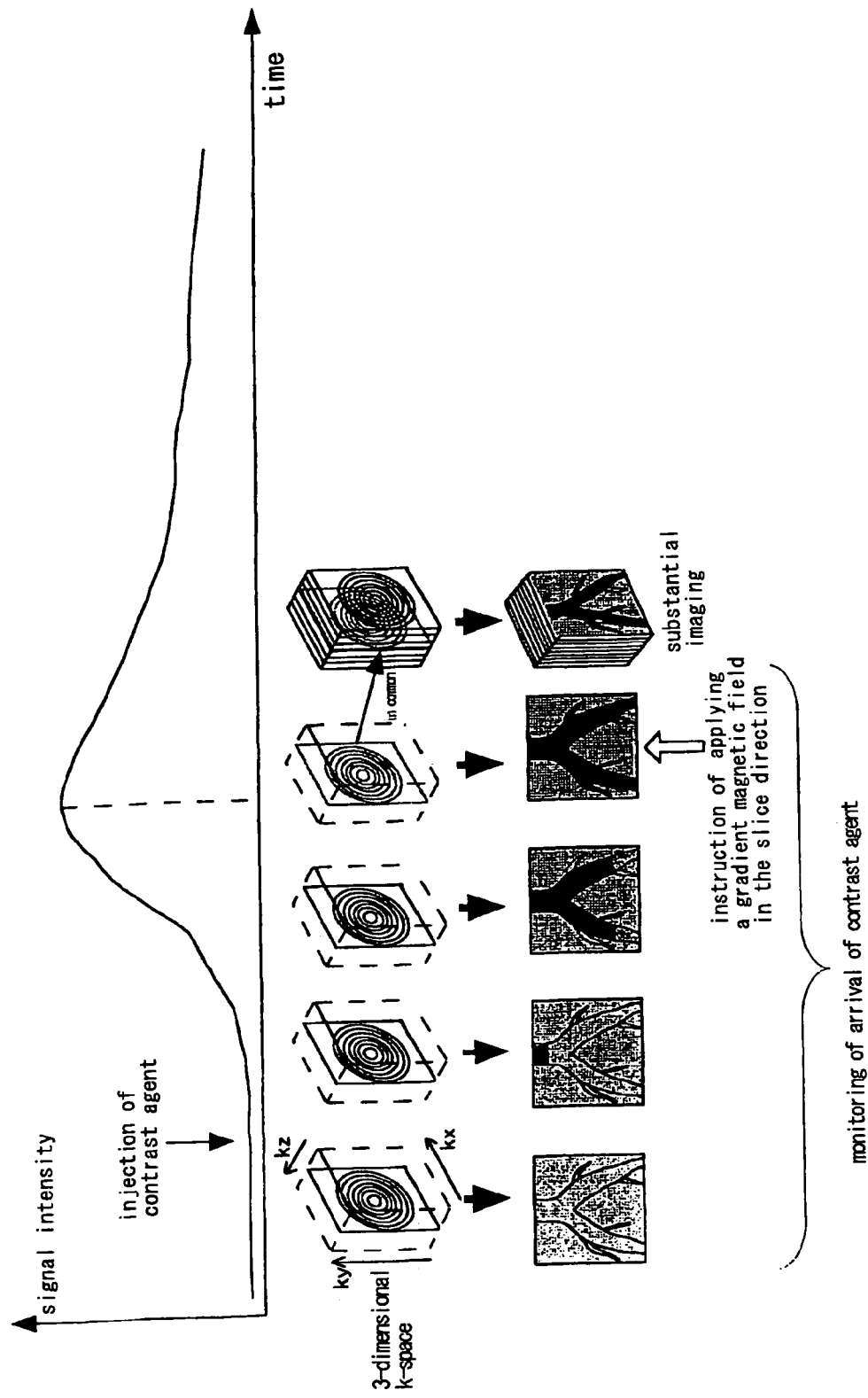
FIG. 2 shows an example of dynamic measurement using an MRI apparatus according to the first embodiment.

Next, blood imaging using the MRI apparatus having the aforementioned configuration will be explained for a three-dimensional measurement. FIG. 2 shows an embodiment of a dynamic measurement, FIG. 3 shows a general gradient-echo type pulse sequence employed in the three-dimensional measurement and FIG. 4 shows a flow of measurement procedures.

The dynamic measurement of this embodiment includes a monitoring mode, which is performed to determine the time for imaging a blood vessel of interest, and a substantial measurement mode, which is imaging of the blood vessel of interest. The two modes are performed in accordance with the same pulse sequence but with different conditions of applying gradient magnetic fields. The monitoring mode is switched to the substantial measurement mode based on the result obtained in the monitoring mode.

Figure 3:
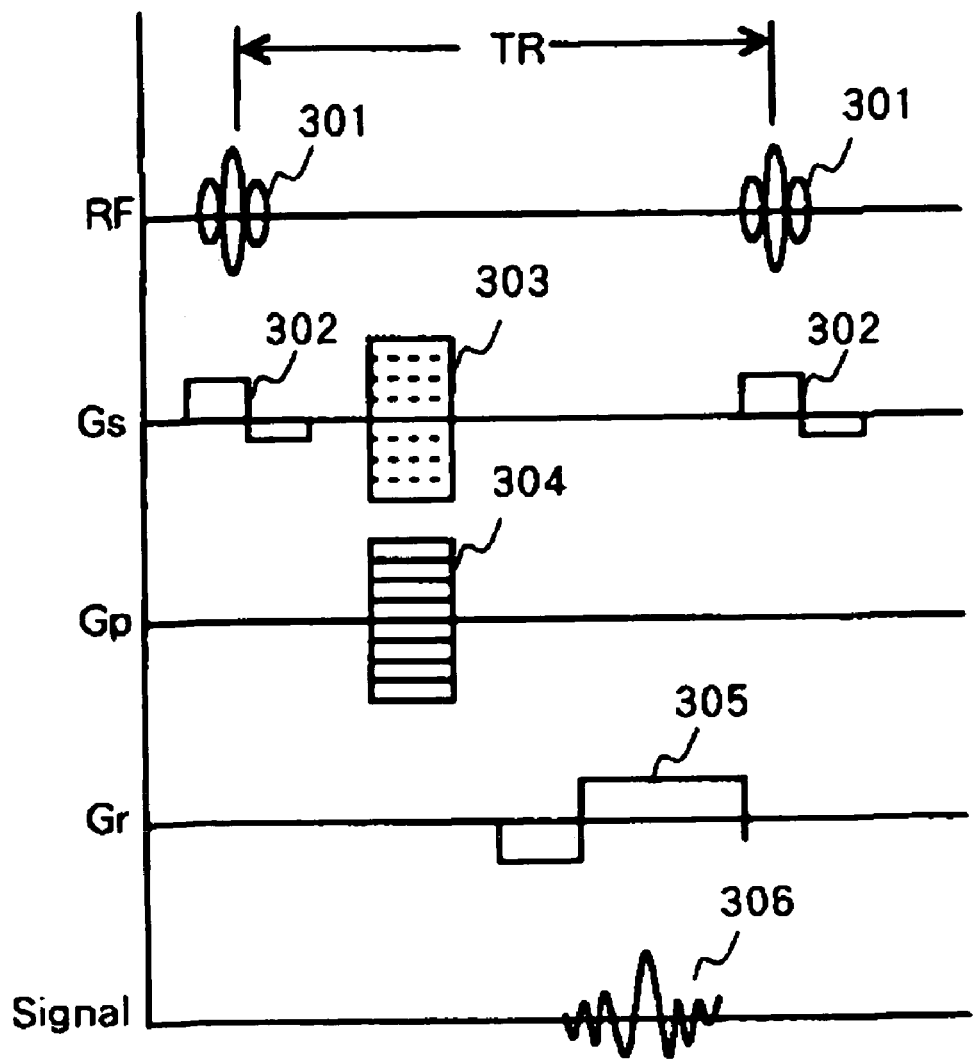
FIG. 3 shows an example of a general pulse sequence used in the dynamic measurement of the present invention.
Figure 4:
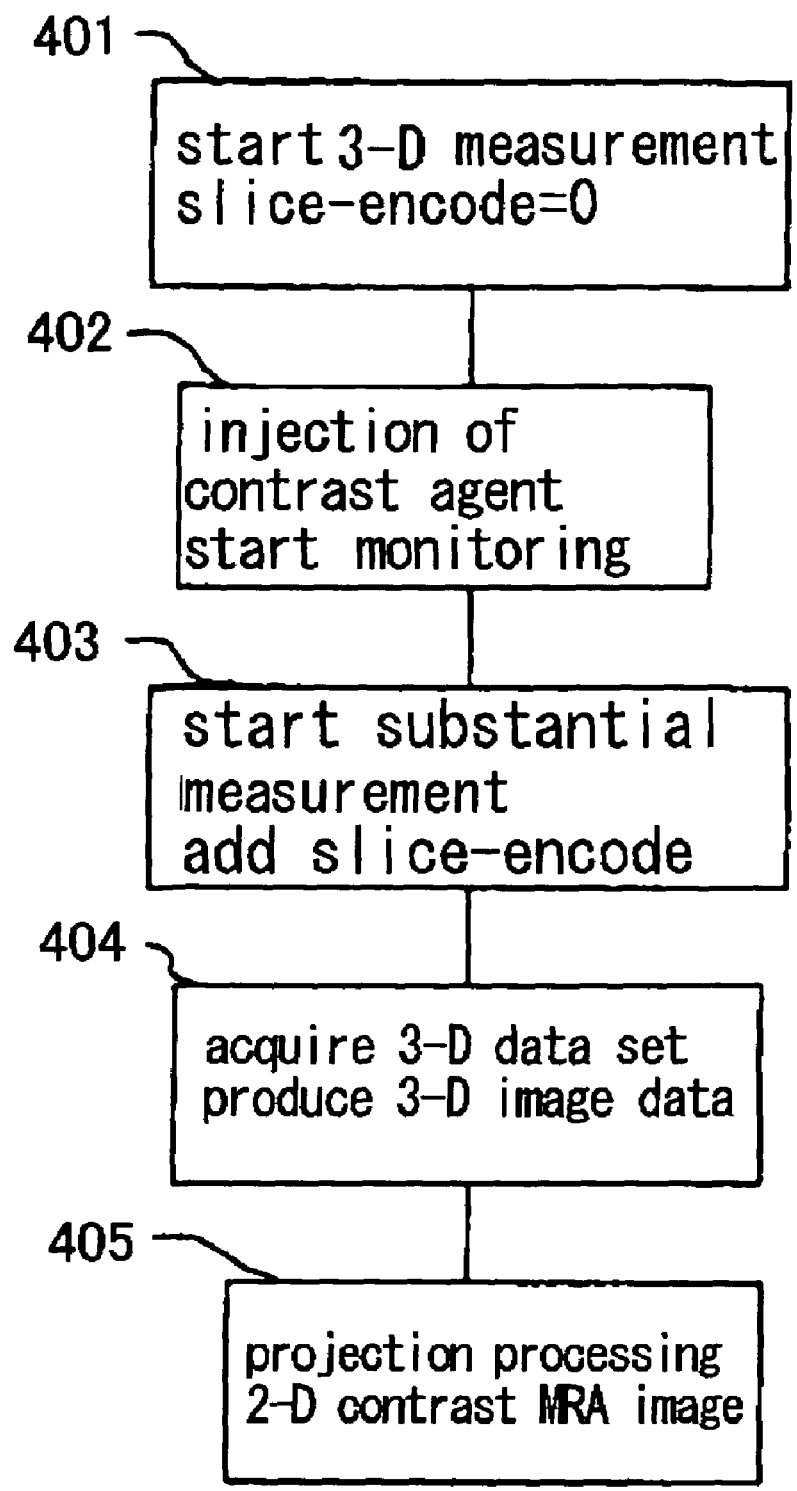
FIG. 4 is a flowchart showing procedures of the dynamic measurement of the present invention.

In the monitoring mode, a pulse sequence of the three-dimensional measurement as shown in FIG. 3 is started prior to injection of a contrast agent (step 401). The pulse sequence is the same as an ordinary gradient-echo type three-dimensional pulse sequence except that no slice-encode is added. Specifically, a region (slab) containing the blood vessel of interest is excited by applying an RF pulse 301 together with a gradient magnetic field 302. Then, a gradient magnetic field 304 in the phase-encode direction is applied and a readout gradient magnetic field 305 is applied to detect an echo signal 306 within a fixed sampling time. Steps from application of the RF pulse 301 to application of the next RF pulse are repeated with a short TR, for example with a repetition time of several milliseconds or several tens of milliseconds while changing the intensity of the phase-encode gradient magnetic fields to collect one set of echo signals phase-encoded differently.

An image is reconstructed using the thus obtained set of echo signals and displayed. Such a measurement is repeated to reconstruct images continuously and update the displayed image. On the other hand, at a desired time after the measurement is started, a contrast agent is injected into a vessel, e.g. antecubital vein of the patient, (step 402) and arrival of the contrast agent is monitored using the time-series image displayed continuously. Since the echo signals acquired in this measurement are generated from the whole slab and are not encoded in the slice direction, the images have low resolution in the slice direction but reflect the whole slab. Accordingly, even if the position of the blood vessel of interest is slightly changed by body movement, the arrival of the contrast agent at the blood vessel of interest can be reliably monitored. In addition, because even a three-dimensional measurement can be carried out in as short time as in a two-dimensional measurement, the image is updated with a high time resolution and the arrival time of the contrast agent can be detected precisely.

When arrival of the contrast agent at the blood vessel of interest has been confirmed, imaging is performed in the substantial measurement mode. The switching can be done automatically or manually. In manual switching, when the user confirms arrival of the contrast agent at the blood vessel of interest by watching a time-series image obtained in the monitoring mode, the user uses the input means 21 to input an instruction to start the substantial measurement. The input can be done through means for inputting a mode-switching instruction (a switching device or GUI) provided in the input means 21.

When the mode is switched automatically, a change in a signal value of the data is monitored by the apparatus. Monitoring of the signal value will be explained with reference to another embodiment in detail but, for example, the signal value is found from the data set acquired by performing the pulse sequence in the monitoring mode and subjected to the one-dimensional Fourier transform, and a time when the signal value or a change of the signal value reaches a predetermined threshold value is determined as the starting time of the substantial measurement. Alternatively, a signal value of an origin of the k-space among the data acquired by performing the pulse sequence in the monitoring mode or a change of the signal value may be monitored.

When the measurement mode has thus been switched to the substantial measurement mode automatically or manually, the CPU 8 alters the condition of applying gradient magnetic fields while repeating the same pulse sequence as in the monitoring mode. In this embodiment, it sends instruction of starting slice encoding to the sequencer 4 (step 403).

Specifically, in the pulse sequence shown in FIG. 3, after the region including a blood vessel of interest is excited by applying an RF pulse 301 together with a gradient magnetic field 302 for selecting the same region as in the monitoring mode, a gradient magnetic field 304 in the phase-encode direction and a gradient magnetic field 303 in the slice-encode direction (shown by a dot line) are applied and then an echo signal 306 is measured. In this case, after a loop (inner loop), in which the gradient magnetic field 303 in the slice-encode direction is fixed and the gradient magnetic field 304 in the phase-encode direction is altered successively, is completed, the loop is repeated with another gradient magnetic field 303 in the slice-encode direction while changing the gradient magnetic field 304 in the phase-encode direction successively. The inner loop is repeated similarly while changing the gradient magnetic field 303 in the slice-encode direction successively to obtain a set of three-dimensional data including all combinations of gradient magnetic fields in the phase-encode direction and gradient magnetic fields in the slice-encode direction.

The Fourier transform is performed on the three-dimensional data set to produce a three-dimensional image-data set (step 404). The three-dimensional image-data set is further subjected to a projection processing to produce a contrast enhanced MRA image (step 405). When the image is reconstructed immediately after the substantial measurement started, the image-data of the displayed image, which is used to determine the starting time of the substantial measurement, is also used for the image reconstruction. The image data is collected at the time when the contrast agent arrives at the blood vessel of interest and can depict the blood vessel of interest well. In addition, the data is collected without applying the gradient magnetic field 303 in the slice direction, that is, the slice-encode is zero. Accordingly, by adding the data of slice-encode 0 to data acquired after beginning of the substantial measurement for image reconstruction, a time for collecting data of slice-encode 0 is omitted in the substantial measurement but an image in which the blood vessel of interest is well depicted can still be obtained.

Thereafter, every time a three-dimensional data set is obtained, three-dimensional image-data is produced and subjected to projection processing to obtain images of a plurality of phases. As the projection processing, a known projection method such as the MIP method in which the maximum value of signal values on a light axis is defined as the blood vessel can be employed.

According to the MRI apparatus of this embodiment, because the same pulse sequence as the substantial measurement pulse sequence but including no slice-encode gradient magnetic field is employed in order to monitor the arrival of the contrast agent, the substantial measurement can be started at the same time when the contrast agent arrives at the blood vessel of interest. As a result, an excellent MRA image can be obtained. In addition, since data collected just before the beginning of the substantial measurement, which reflects the arrival of the contrast agent, is used for producing the substantial measurement image, an MRA image in which the blood vessel of interest is well depicted can be displayed in a short time.

Although it was explained regarding the above embodiment that the slice-encoding gradient magnetic field is omitted in the pulse sequence of the monitoring mode, the pulse sequence of the monitoring mode may be carried out using a slice-encoding gradient magnetic field of a constant encode amount, preferably an encode amount close to zero. Alternately, instead of the slice-encode gradient magnetic field, the phase-encode amount of the phase-encode gradient magnetic field may be fixed at zero or a constant value. Further, the manner of controlling the slice-encode and phase-encode (control of a gradient magnetic field application order) in the substantial measurement is not limited to the illustrated case but an arbitrary ordering may be employed.

Although it was explained that an image is produced using only the image-data measured after the contrast agent is injected, a projection image may be produced by using difference between three-dimensional images measured before and after the contrast agent is injected in case that the body movement is very small or not problematic because of breath-stopping. Use of difference data can suppress the signal intensity of tissues other than the blood vessel and improve the contrast of the blood vessel. The subtraction processing is carried out between the three-dimensional data in the same slice position. Although the subtraction of complexes is preferable, absolute values may be subtracted or data for reconstruction may be subjected to a complex subtraction and reconstruction.

A second embodiment of the MRI apparatus of the present invention will be explained hereinafter. The configuration of the MRI apparatus is similar to that shown in FIG. 1. In this embodiment, however, the signal processing unit 7 has a function of calculating a time intensity curve (TIC) for the detected echo signals and displaying TIC as a graph.

Figure 5:
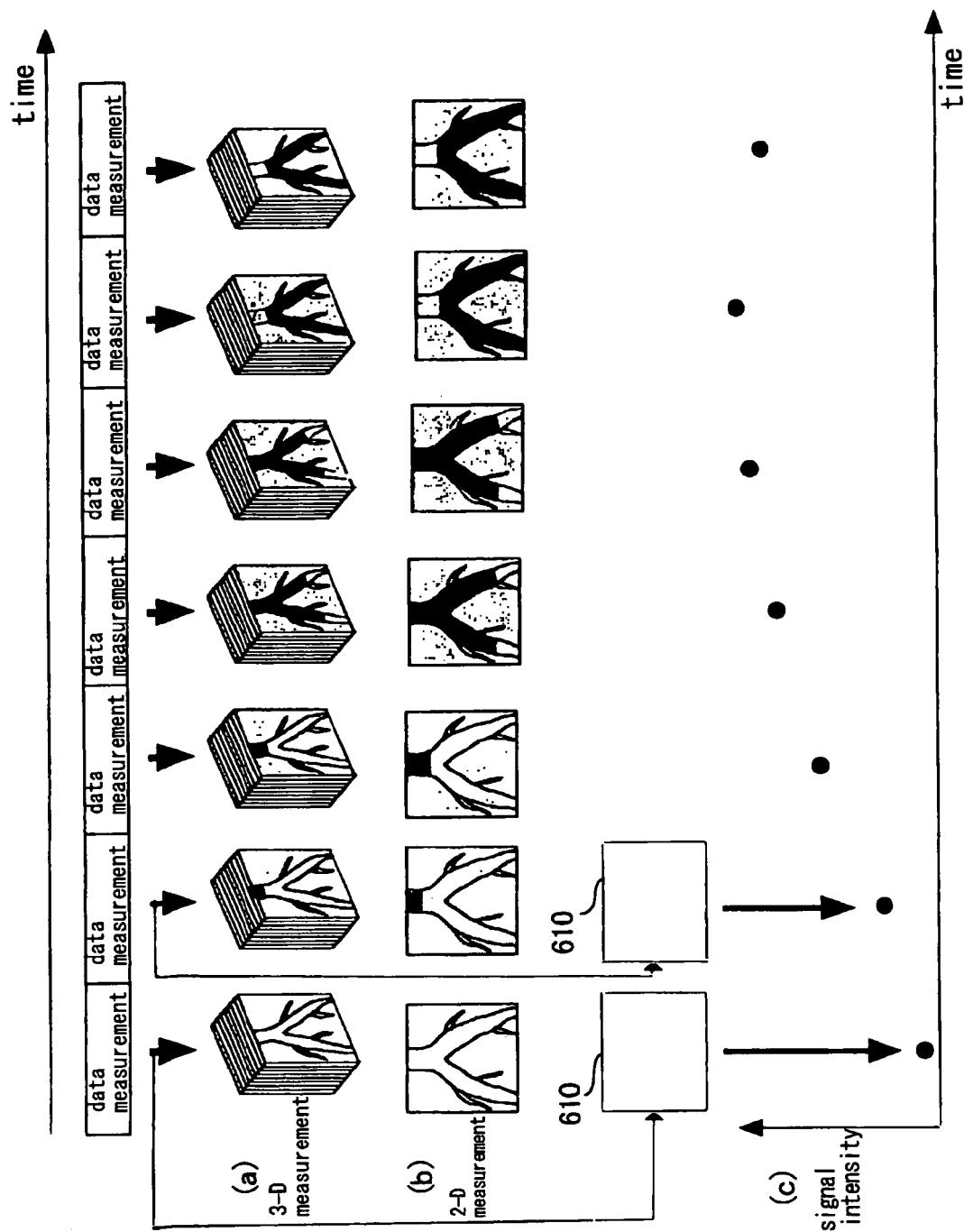
FIG. 5 shows an example of a dynamic measurement using an MRI apparatus according to the second embodiment.
Figure 6:
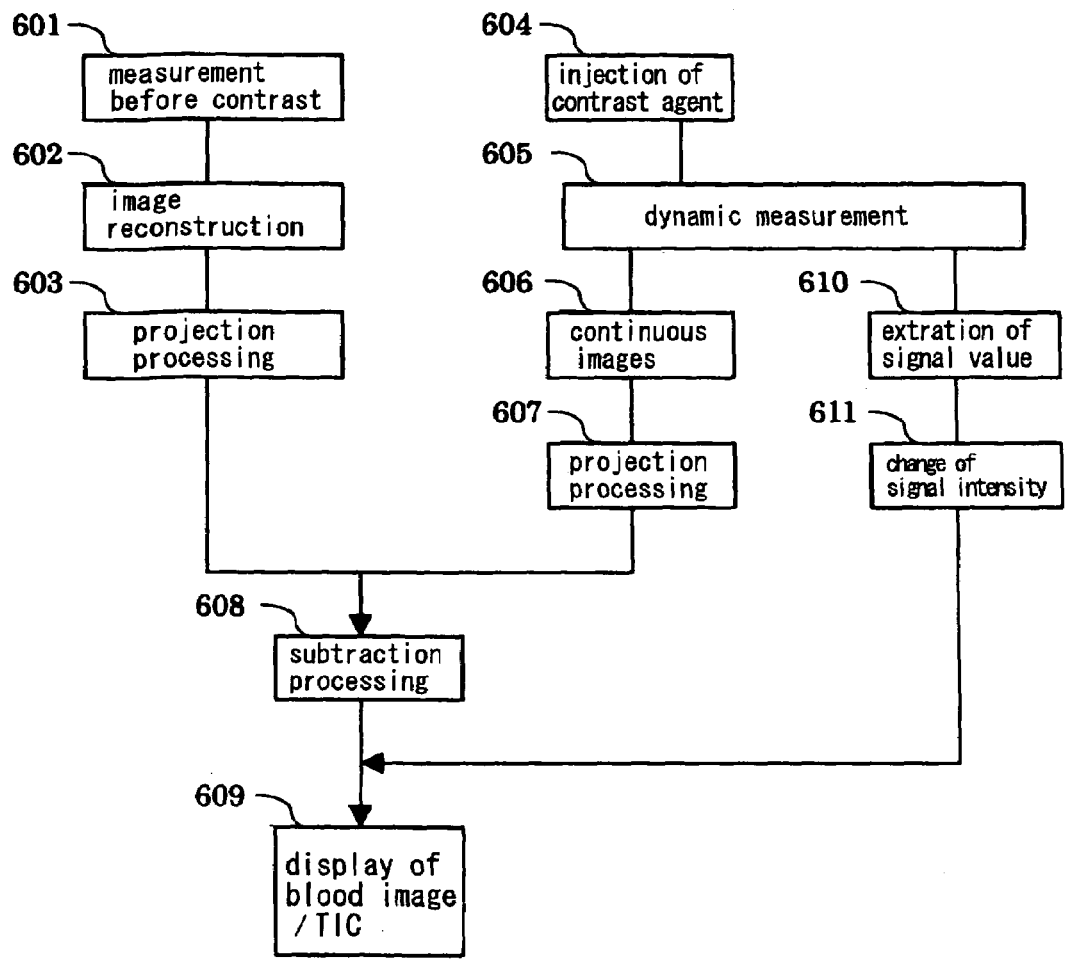
FIG. 6 is a flowchart showing procedures of the dynamic measurement of the second embodiment.

The three-dimensional imaging of the blood vessel using this MRI apparatus will be explained. FIG. 5 shows an embodiment of a dynamic measurement and FIG. 6 is a flowchart showing the procedures.

First, a three-dimensional measurement is conducted without using a contrast agent to obtain three-dimensional data before injection and two-dimensional projection image data using it (steps 601-603). Next, the contrast agent is injected into a predetermined blood vessel of the examined object, for example, an antecubital vein (step 604), and a dynamic measurement is started (step 605).

In measurements performed before and after injection of the contrast agent, a known gradient-echo type pulse sequence as shown in FIG. 3 is carried out with a predetermined slice-encode number and a phase-encode number. However, at the beginning of a measurement conducted after injection of the contrast agent, these encode numbers are set to a small number, for example, half of the encode numbers required for an ordinary blood imaging, to obtain an image having a low spatial resolution. Such a measurement of acquiring three-dimensional data is repeated to obtain time-series data shown in FIG. 5(a) (step 606). Since the time-series data are acquired using a small encode number, they have a low spatial resolution but a high time resolution and contain information of the whole slab including the blood vessel of interest.

Every time the three-dimensional data set is obtained, three-dimensional image-data is produced by the Fourier transform and a two-dimensional blood vessel projection image as shown in FIG. 5(b) is produced by projection processing (step 607). As the projection processing, a known projection method such as the MIP method in which the maximum value of signal values on a light axis is defined as the blood vessel can be employed. This two-dimensional blood vessel projection image and the previous two-dimensional blood vessel projection image obtained before injection of the contrast agent in step 603 are subjected to subtraction (step 608) and the resulting blood vessel image is displayed on the display (step 609).

Apart from such image production, processing for extracting signal values from the time-series three-dimensional data measured continuously is performed (step 610). Concretely, a signal value of origin (kz=0,ky=0,kx=0) of the k-space, in which echo signals are arranged with slice-encode as kz and phase-encode as ky, is selected as an extracted signal value. Alternately, data of kz=0 and ky=0 are added in the readout direction to be defined as an extracted signal value. Specifically, in the pulse sequence shown in FIG. 3, a signal value of an echo signal collected when both of the slice gradient magnetic field 303 and phase-encode gradient magnetic field 304 are zero, or an integral value of the Fourier transform of the echo signal in the readout direction is selected as the extracted signal value. Since data of the origin of the k-space includes the most contrast information of an image obtained from the three-dimensional data, the signal intensity change of this data is a good index of the change of signal intensity enhanced by the contrast agent.

As the extracted signal value, there may be used a difference from the value obtained at the beginning of a measurement such as, for example, a difference between a signal value of the origin of the k-space of data acquired first after the beginning of a measurement and a signal value of the origin of the k-space of data acquired thereafter, or a difference between an integral value of a frequency direction line including the origin of the k-space of data acquired first after the beginning of a measurement and an integral value of a frequency direction line including the origin of the k-space of data acquired thereafter. Use of difference data suppresses signals from unnecessary tissues (tissues other than the blood vessel).

The extracted signal value is found every time an echo signal of the origin is detected in the dynamic measurement and its temporal variation is displayed on the display as shown in FIG. 5(c). Since the thus produced signal intensity curve (TIC) is a graph in which a signal value of raw data or an integral value of the Fourier transform of the raw data in the readout direction is plotted on the time axis, it is displayed without delay after measurement. Accordingly, the user can observe the signal intensity change in real time and start the substantial measurement without delay after the contrast agent arrives at the blood vessel of interest by reference to the displayed TIC. In the substantial measurement, a three-dimensional measurement of high spatial resolution, in which one or both of the slice-encode number and the phase-encode number is increased, is performed to depict the region with a high spatial resolution after arrival of the contrast agent.

In this embodiment, switching from the monitoring mode to the substantial measurement mode may be done by the user sending an instruction to CPU 8 via the input means while observing the TIC displayed on the display device or may be determined automatically by the CPU 8 based on a predetermined threshold for the extracted signal value together with predetermined conditions of low-spatial resolution measurement and high-spatial measurement. Not only switching of mode but also end of measurement can be determined by watching the TIC.

Figure 7:
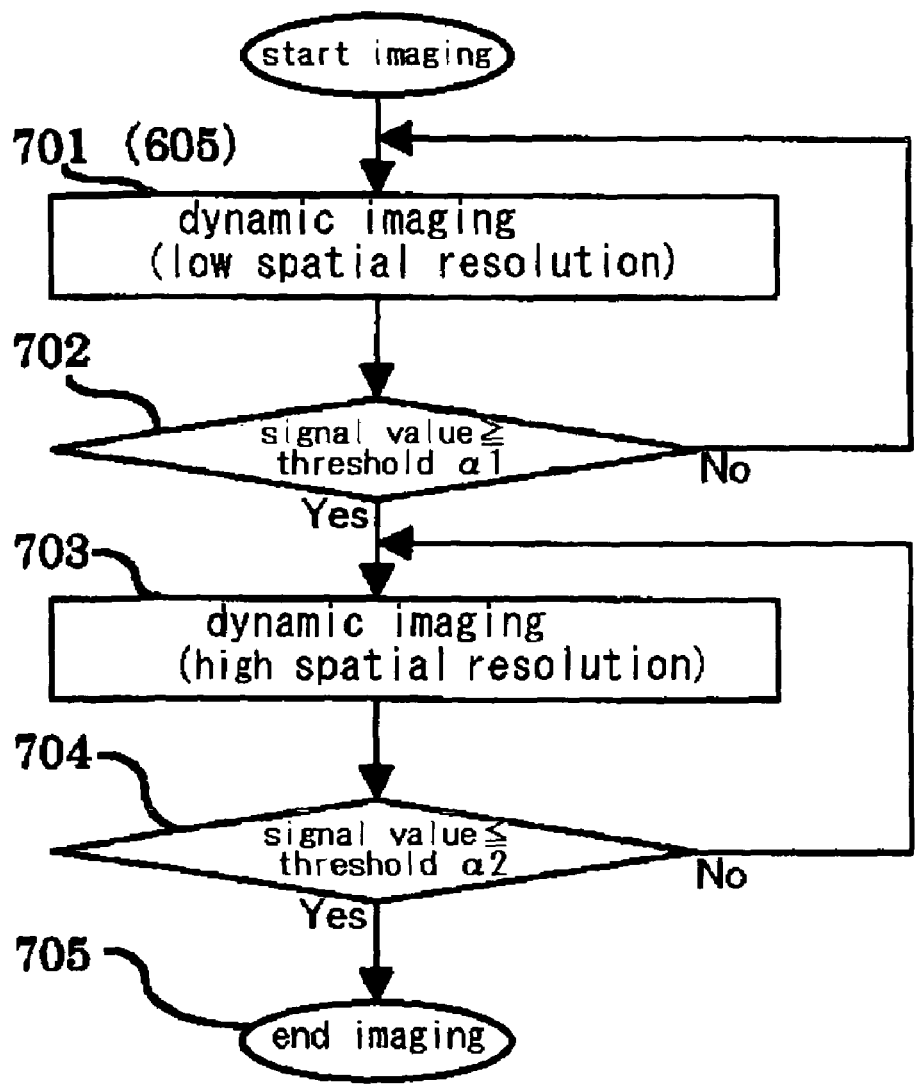
FIG. 7 shows another example of a dynamic measurement using an MRI apparatus according to the second embodiment.

Such an embodiment is shown in FIG. 7. In this embodiment, two threshold values, $\alpha 1$ for switching measurement mode and $\alpha 2$ for ending measurement, are set. Once a measurement is started, while dynamic imaging is performed under a condition of applying gradient magnetic fields of low spatial resolution in the monitoring mode (step 701), extraction of a signal value is carried out. The dynamic imaging in the monitoring mode is repeated until the signal value arrives at the predetermined threshold $\alpha 1$. When the signal value reaches the predetermined threshold $\alpha 1$ (step 702), it is regarded as arrival of the contrast agent at an imaging region, and the condition of applying the gradient magnetic fields is altered from the low spatial resolution condition to the high spatial resolution condition and the substantial measurement is started (step 703). In the substantial measurement, extraction of the signal value and imaging in the substantial measurement mode are continued until the extracted signal value reaches the predetermined threshold $\alpha 2$. When the signal value reaches the predetermined threshold $\alpha 2$ (step 704), it is regarded as flow-out of the contrast agent, and imaging is finished (step 705).

According to the second embodiment, a signal value is found and displayed in parallel with continuous imaging by the dynamic measurement and then arrival of the contrast agent at the blood vessel of interest can be detected accurately in real time. In addition, imaging of low spatial resolution but high time resolution can be carried out until the contrast agent arrives at the blood vessel of interest and imaging of high time resolution for well depicting the blood vessel can be carried out after the contrast agent arrives at the blood vessel of interest.

Although a three-dimensional measurement was explained regarding the above embodiment, the present invention can be applied to a two-dimensional measurement.

According to the present invention, the substantial measurement can be started with proper timing in a dynamic MRA using a contrast agent. As a result, the region of interest is imaged while the contrast agent resides in the region to produce an excellent blood vessel image. In addition, because the image data used in the monitoring mode can be used also as a part of image data for the substantial measurement, data obtained at a time when the contrast agent density reaches its maximum value can be utilized to produce excellent time-series images without delay in displaying them.

The invention claimed is:

1. A magnetic resonance imaging apparatus comprising an imaging means for applying high-frequency magnetic fields and gradient magnetic fields to an object in a static magnetic field, in accordance with a pulse sequence for dynamic measurement for continuously obtaining a plurality of time-series images, and for measuring NMR signals emitted from the object, a signal processing means for forming images of a desired tissue of the object, from the NMR signals, a display means for displaying the images and a control means for controlling the imaging means and the signal processing means;
   wherein said imaging means is provided with a two-dimensional monitoring mode in which a desired slab of the object is measured using a pulse sequence for the dynamic measurement under a condition of applying gradient magnetic fields with a low spatial resolution, and is provided with a three-dimensional measurement mode in which the same slab is measured using the same pulse sequence under a condition of applying gradient magnetic fields with a high spatial resolution, and
   said control means includes mode switching means for switching from the two-dimensional monitoring mode to the three-dimensional measurement mode, and
   said switching means switches the two-dimensional monitoring mode to the three-dimensional measurement mode with desired timing when the two-dimensional monitoring mode is performed, and
   wherein the dynamic measurement performed by said imaging means is blood imaging for observing a change of blood flow using a contrast agent, where slice encode is omitted in the two-dimensional monitoring mode to obtain two-dimensional images and the slice encode is added in the three-dimensional measurement mode to obtain three-dimensional images,
   wherein said control means controls said signal processing means to reconstruct images immediately after the three-dimensional measurement mode begins, using data including data acquired in the pulse sequence performed without the slice encode just before the three-dimensional measurement.

2. The magnetic resonance imaging apparatus of claim 1, wherein data of the time-series images is three-dimensional data and is transformed to a two-dimensional projected image to be displayed on said display means.

3. The magnetic resonance imaging apparatus of claim 1, wherein said mode switching means has an input means for mode switching, and the two-dimensional monitoring mode is switched to the three-dimensional measurement mode by directly inputting a switching instruction to said mode switching means.

4. The magnetic resonance imaging apparatus of claim 1, wherein the control means sends an instruction to the mode switching means to indicate starting time of the three-dimensional measurement mode based on signal intensity of data acquired when the pulse sequence is applied without slice encode.

5. The magnetic resonance imaging apparatus of claim 1, wherein the apparatus is provided with means for extracting reference data from the dynamic measurement data acquired in the monitoring mode, and a temporal change of the extracted reference data is displayed on said displaying means.

6. The magnetic resonance imaging apparatus of claim 5, wherein the desired timing for switching by said mode switching means from the two-dimensional monitoring mode to the three-dimensional measurement mode includes a timing when the change of the reference data exceeds a predetermined threshold value.

7. The magnetic resonance imaging apparatus of claim 5, wherein said mode switching means finishes the three-dimensional measurement mode when the extracted reference data or the change of the reference data reaches a predetermined threshold value.

8. The magnetic resonance imaging apparatus of claim 5, wherein the desired timing for switching by said mode switching means from the two-dimensional monitoring mode to the three-dimensional measurement mode includes a timing when the extracted reference data reaches a predetermined threshold value.

9. The magnetic resonance imaging apparatus of claim 5 or claim 8, wherein the reference data is a signal value at an origin of a k-space among the NMR signals acquired in the monitoring mode or an integration of data in a frequency encoding direction including the origin of the k-space.

10. The magnetic resonance imaging apparatus of claim 5 or claim 8, wherein the reference data is a difference of a signal value at an origin a k-space among the NMR signals acquired in the monitoring mode or an integration of data in a frequency encoding direction including the origin of the k-space from the corresponding value acquired at the beginning of the monitoring mode.

11. A magnetic resonance imaging apparatus comprising an imaging means for applying high-frequency magnetic fields and gradient magnetic fields to an object in a static magnetic field in accordance with a pulse sequence for dynamic measurement for continuously obtaining a plurality of time-series images, and for measuring NMR signals emitted from the object, signal processing means for forming images of a desired tissue of the object from the NMR signals, a display means for displaying the images and a control means for controlling the imaging means and the signal processing means, wherein said imaging means is provided with a two-dimensional monitoring mode in which a desired slab of the object is measured using a pulse sequence for the dynamic measurement under a condition of applying gradient magnetic fields with a low spatial resolution and a three-dimensional measurement mode in which the same slab is measured using the same pulse sequence under a condition of applying gradient magnetic fields with a high spatial resolution, said control means has a mode switching means for switching from the two-dimensional monitoring mode to the three-dimensional measurement mode, and said switching means switches the two-dimensional monitoring mode to the three-dimensional measurement mode with desired timing when the two-dimensional monitoring mode is performed, and the gradient magnetic fields include a slice encode, a phase encode and a frequency encode for the two-dimensional or three dimensional measurement, and under the condition of applying gradient magnetic fields with low spatial resolution in the two-dimensional monitoring mode one of the slice encode and the phase encode is omitted and under the condition of applying gradient magnetic fields with high spatial resolution in the three-dimensional measurement mode both of the slice encode and the phase encode is imparted, wherein said control means controls said signal processing means to reconstruct images immediately after the three-dimensional measurement mode begins, using data including data acquired in the pulse sequence performed without the slice encode or the phase encode just before the three-dimensional measurement.

12. The magnetic resonance imaging apparatus of claim 11, wherein a difference image between blood images acquired before and after injection of a contrast agent is displayed on said displaying means.

* * * * *